United States Patent [19]

Gulla et al.

[11] 4,324,589
[45] Apr. 13, 1982

[54] SOLUTE MONITORING PROCESS

[75] Inventors: Michael Gulla, Sherborn, Mass.; Barry J. Hartnett, Nashua, N.H.

[73] Assignee: Shipley Company Inc., Newton, Mass.

[21] Appl. No.: 116,579

[22] Filed: Jan. 29, 1980

Related U.S. Application Data

[62] Division of Ser. No. 9,542, Feb. 5, 1979, Pat. No. 4,229,218.

[51] Int. Cl.$^3$ .............................................. C23C 3/02
[52] U.S. Cl. ................................ 106/1.22; 23/230 A; 106/1.23; 106/1.26; 106/1.27; 427/443.1; 427/437; 427/438
[58] Field of Search .................. 106/1.22, 1.23, 1.26, 106/1.27; 427/443.1, 437, 438; 23/230 A

[56] References Cited

U.S. PATENT DOCUMENTS

| | | | |
|---|---|---|---|
| 3,532,519 | 10/1970 | Hirohata et al. | 106/1.23 |
| 3,650,957 | 3/1972 | Shipley et al. | 252/79.1 |
| 3,728,137 | 4/1973 | Shipley et al. | 106/1.26 |
| 3,951,602 | 4/1976 | Thompson | 23/230 R |
| 4,002,786 | 1/1977 | Hirohata et al. | 427/443.1 |
| 4,096,301 | 6/1978 | Slominski et al. | 427/443.1 |

OTHER PUBLICATIONS

Kirk–Othmer, *Encyclopedia of Chem. Tech.*, Sec. Ed., vol. 5, pp. 791 & 792.
Rhael, E., *Color and Instrumentation*, Sandoz Inc., New York, pp. 1–55.
Shipley, Cuposit 7012 Copper Color Indicator System, 3/74.
Shipley, Analysis of Copper Baths Using Shipley Comparator, 9/74.
Shipley, Analysis of Electroless Nickel Baths Using Shipley Comparator, 4/76.
Shipley, Shipley Comparators, 5/76.

*Primary Examiner*—Lorenzo B. Hayes
*Attorney, Agent, or Firm*—Robert L. Goldberg

[57] ABSTRACT

This invention relates to monitoring the concentration of a component dissolved in solution where the component imparts a perceptible color to the solution and varies in concentration with use of the solution.

32 Claims, 8 Drawing Figures

SOLUTE MONITORING PROCESS

This is a division of application Ser. No. 009,542 filed Feb. 5, 1979 now U.S. Pat. No. 4,229,218.

The invention is based upon use of a colorant of a fixed optical density that absorbs light in a different region of the visible spectrum than the monitored component. As the monitored component varies in concentration with use of the solution, the optical density of that component in solution varies as a function of its concentration and consequently, the amount of light, i.e., the intensity of light, passing through the solution will also vary as a function of concentration. Since the optical density of the colorant remains fixed during use, the optical density of the monitored component changes relative to the optical density of the colorant during use of the solution. Because the monitored component and colorant absorb light in different regions of the visible spectrum and their optical densities change relative to each other, there results a perceptible color change as a function of concentration that may be seen visually or measured by instrumentation.

BACKGROUND OF THE INVENTION

1. Introduction

This invention relates to monitoring the concentration of a component dissolved in solution as its concentration varies with use of the solution.

2. Description of Prior Art

Many solutions contain dissolved components which vary in concentration with use of the solution. For such solutions, it is frequently desirable or necessary to periodically or continuously determine the concentration of a solution component undergoing concentration change. For example, when the concentration of a component undergoing change reaches a given pre-determined level, there may be a need to replenish or remove the ingredient so that its concentration is returned to its approximate initial level. The need for replenishment is especially true with metal plating solutions, typically electroless metal plating solutions such as those illustrated in U.S. Pat. Nos. 3,728,137 (for electroless copper) and 3,719,508 (for electroless nickel), both incorporated herein by reference. For such solutions, as the plating metal is consumed by deposition over a substrate, the properties of the solution are altered such as by a decrease in the plating rate and a change in deposit properties. To avoid such changes, these solutions are periodically replenished whereby consumable ingredients, such as the plating metal, are returned to their initial concentration levels. For solutions used to etch metal, for example, such as those disclosed in U.S. Pat. No. 3,650,957 (for the etching of copper), incorporated herein by reference, when the concentration of the etched metal builds to an undesirably high level, the etch rate may decrease and undesired deposits may form on the etched surface. To prevent these changes in the properties of the etchants, it is desirable to periodically remove a portion of the etched metal by methods known to the art.

Using metal plating solutions for purposes of illustration, it is known that the concentration of the components of such solutions may be periodically monitored by chemical analysis and, in some cases, by continuous analysis using sophisticated analytical instrumentation as illustrated in U.S. Pat. Nos. 3,532,519; 3,951,602; 4,002,786 and 4,096,301, all incorporated herein by reference. Monitoring the concentration of consumable solution components using sophisticated instrumentation frequently requires trained technicians and costly investment in instrumentation. Both are impractical or prohibitively expensive for small plating shops and are frequently unnecessary for larger plating installations where precise control of solution components for good quality plating is not required. For all such installations, it is desirable to provide a low-cost system for effectively monitoring the concentration of critical components in solution which undergo change in concentration during use of the solution which system can be easily used by non-technically trained operators.

One system known in the art for monitoring the concentration of cooper in a copper plating solution is a copper color indicator kit marketed by Shipley Company Inc. which uses a set of color standards, a solution of dye and a simple device called a "color comparator". Using this system, approximate copper concentration in a copper plating solution is determined by taking a 20 ml sample from the plating bath and adding the same to 60 ml of Cuposit® 7012 copper color indicator, an aqueous solution of methyl orange. The resulting mixture is visibly compared with a set of colored standards using the color comparator, and the replenishment of the plating bath is made in accordance with a replenishment table for the specific copper solution in use.

Although useful, the color comparator suffers several problems in that it requires the operator to take a sample from the plating solution and perform several steps to determine required replenishment. Errors are easily introduced because of the small size of the sample being used and the relatively large volume differences between the color indicator and the solution sample. Therefore, though low in cost, such a system is easily mis-used, especially in the hands of a careless or untrained operator.

Ideally, it would be desirable to provide a plating solution where the concentration of the plating metal may be monitored by observing the solution or by taking a sample of the solution and comparing it to a permanent set of standards without any additional manipulative steps. Such a system would permit a relatively untrained operator to determine concentration of a component undergoing concentration change at any time during use of the solution by looking at the bath or by sampling the bath without the necessity for accurate measurements or other manipulative steps except, perhaps, placing a sample in a simple instrument, without mixing, for better accuracy, if desired.

SUMMARY OF THE INVENTION

The subject invention provides a simple, colorimetric procedure for monitoring the concentration of a colored component in solution that varies in concentration as the solution is used. The invention is especially useful for monitoring the concentration of the metal content of an electroless metal plating solution.

The component to be monitored in accordance with the invention must impart a color to the solution—that is, the solution containing the component has spectral absorption properties whereby white light has a portion of its visible spectrum absorbed and another portion transmitted so that the solution appears to possess a perceptible color. Since optical density of a solution is a function of concentration of the absorbing species, the optical density of the solution will vary with the concentration of the component undergoing concentration change during use of the solution and therefore, the amount of light transmitted through the solution will also vary as a function of concentration.

To monitor the concentration of the component undergoing change (hereafter the "monitored component"), there is used a colorant that absorbs a portion of the visible spectrum that is different from that portion of the spectrum absorbed by the monitored component, preferably, a colorant that is a color complement of the monitored component. The colorant is used in a manner whereby its optical density remains fixed during use of the solution. The result is a change in the optical density of the monitored component as a function of its concentration relative to a constant optical density for the colorant. Since they possess different absorption properties and therefore transmit light at different wavelengths, there is a perceptible color change in the transmitted light as a function of the concentration of the monitored component.

DESCRIPTION OF THE PREFERRED EMBODIMENTS

For purposes of illustration, the following description will demonstrate the invention used to monitor components in an electroless metal plating solution though it should be understood that the invention has substantially broader application as will be described in greater detail further in the specification.

An electroless copper plating solution contains as principal ingredients a copper salt, a reducing agent for the copper such as formaldehyde, a complexing agent to hold copper in solution and a source of hydroxide. The principal chemical reaction controlling the plate-out of copper from solution onto a receptive surface is well known and may be represented by the following equation:

Based upon the equation, it is shown that three ingredients are consumed during use - copper, formaldehyde and hydroxide and the three react in a given stoichiometric ratio to yield the copper plate.

An electroless nickel plating solution contains as principal ingredients a nickel salt, a reducing agent for the nickel salt, typically a hypophosphite, a complexing agent to hold the nickel in solution and a pH adjustor. The principal reaction controlling nickel plate-out is equally well known and may be represented by the following equation:

The above equation shows that, as with copper solutions, three ingredients are consumed during use of the solution—nickel, hypophosphite and the pH adjustor and that the three react in a given stoichiometric ratio to yield the nickel plate.

The plating metal in solution in the relatively high concentrations used and complexed with the complexing agent gives the solution an intense color—royal blue for a copper plating solution and green for a nickel plating solution. Consequently, the metal in solution is the colored component in varying concentration that is monitored in accordance with the procedures of this invention.

From the equations illustrating the principal chemical reaction for copper and nickel solutions, monitoring the concentration of the metal as the solution is used for plating not only gives metal construction, but based upon the stoichiometry, the consumption of metal is a guide to the consumption of reducing agent and pH adjustor. In practice, however, side reactions take place that consume the other ingredients to some extent beyond the consumption from the plating reaction and therefore, reliance upon stoichiometry alone cannot be used to formulate a replenishment schedule, though with experience in the use of a particular solution, a correlation between metal consumption and the consumption of other ingredients can be made. Consequently, the ability to monitor the metal content is an important tool in the use of the plating solution because it not only permits replenishment of the metal values as necessary, but with appropriate considerations for side reactions, may also be used as a guide to replenishment of the other consumable solution components.

Figure 1:
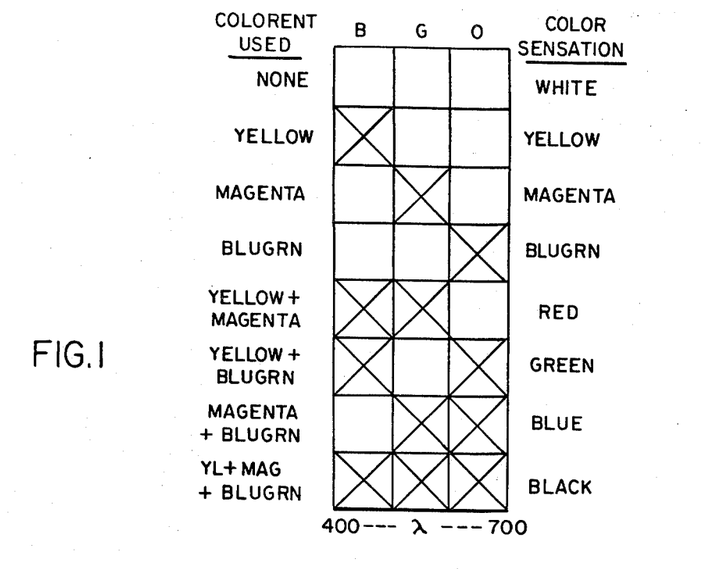
FIG. 1 is a chart of color perception as a consequence of absorption by colorants.

The present invention utilizes the light absorption properties of the monitored component to determine its concentration at any time during use of the solution. In this respect, it is known that absorption within portions of the visible spectrum of white light passing through solution results in the perception of a given color. This is illustrated in FIG. 1 of the drawings which is a representation of color sensation or perception as a consequence of absorption by colorants contained in solution in unit volume—i.e., where more than one colorant is used in solution, each is used in an amount sufficient to absorb light of a given wave length equally. FIG. 1 illustrates that where no colorant is present, white light passing through solution appears white because no portion of the visible spectrum is absorbed by the solution. When a single colorant is added, there is absorption usually in one portion of the visible spectrum. Using a yellow colorant for purposes of illustration, yellow absorbs in the blue region while green and red are transmitted. The mixture of green and red results in the perception of yellow. When more than one colorant is used, and where each absorbs in a different region, there is absorption in several regions of the visible spectrum. For purposes of illustration, again with reference to FIG. 1, a mixture of yellow colorant and a blue-green colorant will appear green because yellow absorbs in the blue region and the blue-green absorbs in the red region resulting in the transmittance of only the green portion of the spectrum.

Figure 2:
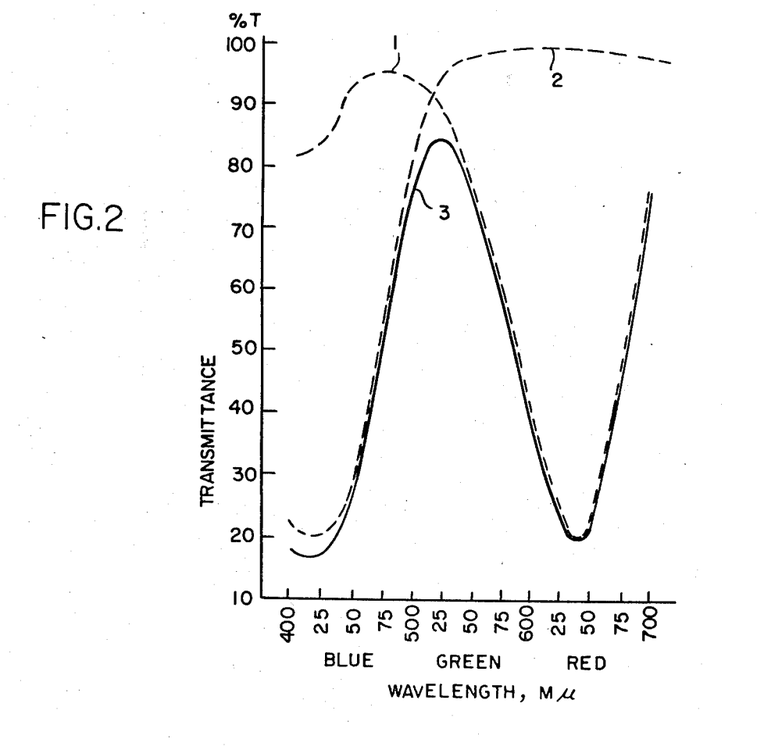
FIG. 2 is a transmittance curve for a yellow colorant, a blue-green colorant and the mixture of the two.

A curve for a mixture of green and yellow colorants in solution is graphically represented in FIG. 2 of the drawings where Curve 1 is the transmittance curve for may be a filter external to the solution that absorbs light at a given desired wave length placed between the light passing through the solution and the eye. If a filter is used, the solution component undergoing change would be monitored by viewing the solution through the filter and observing color change. Alternatively, the colorant may be added directly to the solution such as by dissolving a dye in solution. Where the colorant is internal, the colorant would be selected not only for its light absorption properties, but also its solubility and chemical properties as well. When added to solution, the colorant should be soluble in solution and should not react adversely with the other reactants contained in solution.

The standard for colorant selection, other than its solubility and chemical reactivity properties, is its spectral absorption properties. The colorant and the monitored component should absorb light in different regions of the visible spectrum to effect color change and preferably are color complements of each other. In this respect, the maximum absorption for the colorant and the monitored component should have a wavelength separation of at least 50 millimicrons and preferably, at least 100 millimicrons. In a preferred embodiment of the invention, the monitored component has its maximum transmittance at a wavelength not greater than 50 millimicrons of the wavelength for maximum absorption of the colorant, preferably not greater than 25 millimicrons and most preferably, at a wavelength substantially coincident with the maximum absorption of the colorant. Coincident of the maximum transmittance for the monitored component with the maximum absorption for the colorant results in a more easily perceived color change as a function of concentration and permits a lower colorant concentration.

With regard to the above, it should be noted that a colorant may absorb in the ultra-violet or infrared portions of the spectrum provided the mixture provides a color change with concentration.

Where the colorant is added directly to the solution, its concentration in solution is dependent upon its optical properties, particularly, the optical density of the solution at the wavelength where there is maximum transmittance in the colorant. For purposes of this invention, it is desirable to use as small a concentration of colorant as possible consistent with the objects of observable color change because most colorants do not participate in the chemical reaction taking place within the solution and, therefore, are in the nature of contaminants. The guidelines for determining the amount of colorant is dependent upon whether the monitored component increases or decreases in concentration during use of the solution. For a solution undergoing a decrease in concentration during use, preferably, the colorant is used in an amount insufficient to cause a substantial color change in the solution to which it is added when the solution is at 100% concentration of the monitored component, but sufficient to cause a perceptible color change when the concentration of the monitored component changes from its initial concentration to a given predetermined level; for example, a 20% decrease from its initial concentration.

For a solution containing a monitored component which increases in concentration during use, the amount of colorant is that amount that provides a solution of a perceptibly different color from the initial color of the solution at a point when the monitored component reaches a predetermined maximum level. For example, an etching solution may be free of monitored component prior to use and, therefore, the colorant will provide an initial color to the solution. Enough colorant should be added so that the solution will have a perceptible different color when the etched component reaches a given predetermined level.

With the above guidelines, an empirical determination of colorant concentration can be used. One method would comprise preparation of two solutions, one containing the monitored component at a predetermined concentration where use of the solution is to terminate and the other containing the monitored component at an initial concentration. Again, using a copper plating solution for purposes of illustration, a first plating solution would be prepared with copper at 100% concentration and a second solution with copper diluted to where it would typically be replenished; for example, at a concentration of 80% of the original copper concentration. Equal amounts of colorant would be added to each solution until enough colorant is added so that the color difference between the solution at 100% and 80% is readily perceived. Using an etching solution for purposes of illustration, two solutions are again used, one with the etchant preferably free of the monitored component and the other containing the monitored component at a concentration where etching is to be terminated. Equal amounts of colorant are added to each until sufficient colorant is added to provide an easily perceived color change between the two.

Where the colorant is external to the solution, such as where a filter is used, concentration is not a consideration, but the same guidelines apply. Consequently, the filter is of an optical density whereby there results an easily perceived color change when the concentration of the monitored component is of a selected predetermined level.

Figure 7:
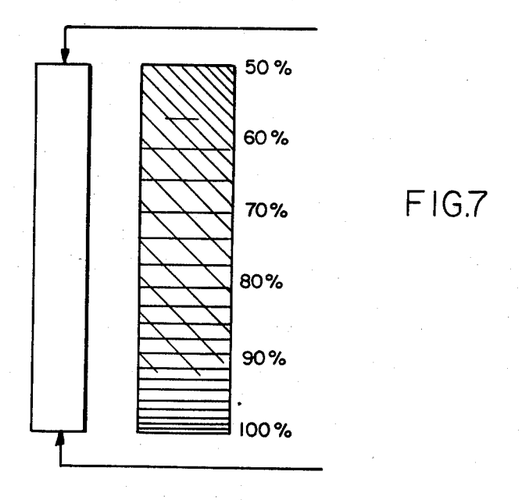
FIG. 7 represents one means for determining component concentration as a function of solution color.

The concentration of the monitored component in solution using a colorant in accordance with the invention may be determined by visual observation, preferably using color standards that correlate color with concentration. For example, in one embodiment of the invention illustrated in FIG. 7 of the drawings, a solution containing a colorant can be monitored by continuously passing a stream of the solution through a colorless viewing tube in proximity to a color chart varying in color correlated to concentration of the monitored component. For the illustrated copper plating solution containing a yellow colorant, the color chart would vary from blue through various shades of green. Matching the solution in the tube with the color of the chart provides a continuous reading on copper concentration. In an alternative embodiment, still with reference to FIG. 7 of the drawings, the tube can be yellow rather than colorless with no colorant added to the solution. The same color chart and correlation would be used.

The invention will be better understood by reference to the following examples.

EXAMPLE 1

Figure 8:
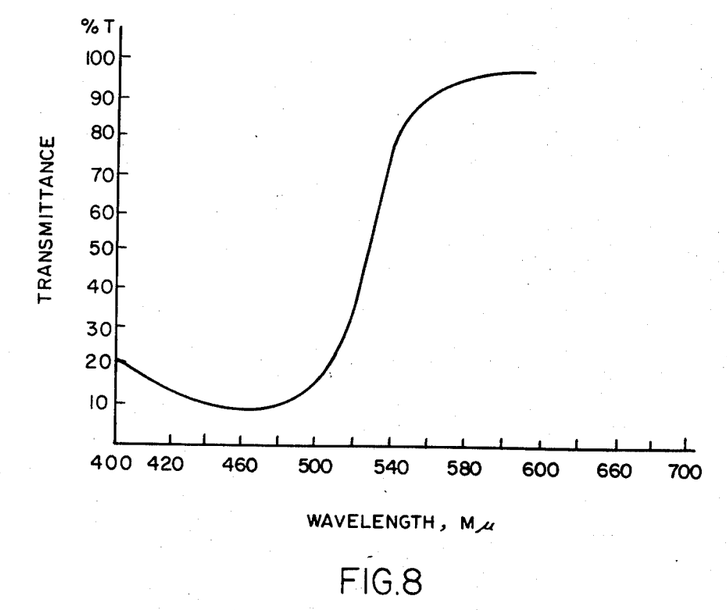
FIG. 8 is a transmittance curve for methyl orange.

Eight ml of a 1% solution of methyl orange in water are added to 1 liter of a copper plating solution having the formulation set forth above. The transmittance curve for methyl orange is represented in FIG. 8 of the drawings. The addition of the methyl orange causes the copper plating solution to turn aquamarine in color. Following the addition of the methyl orange, the solution is used at room temperature to plate catalyzed epoxy boards in a loading of about 0.25 square feet per a solution of Xylene Blue AS, Curve 2 is the transmittance curve for a solution of Xylene Light Yellow R and Curve 3 is the transmittance curve for the mixture of the two. The yellow dye suppresses the transmittance of blue and violet light which would otherwide be transmitted by the Xylene Blue AS solution while the blue-green component suppresses the orange and red light which would otherwise be transmitted by the Xylene Light Yellow R, leaving only the green component of the illuminant, which is passed by both colorants, to be transmitted.

Using a copper plating solution for purposes of illustration, complexed copper in solution has maximum absorption properties in the red region and maximum transmittance properties in the blue region so that a copper plating solution is perceived as blue.

Figure 3:
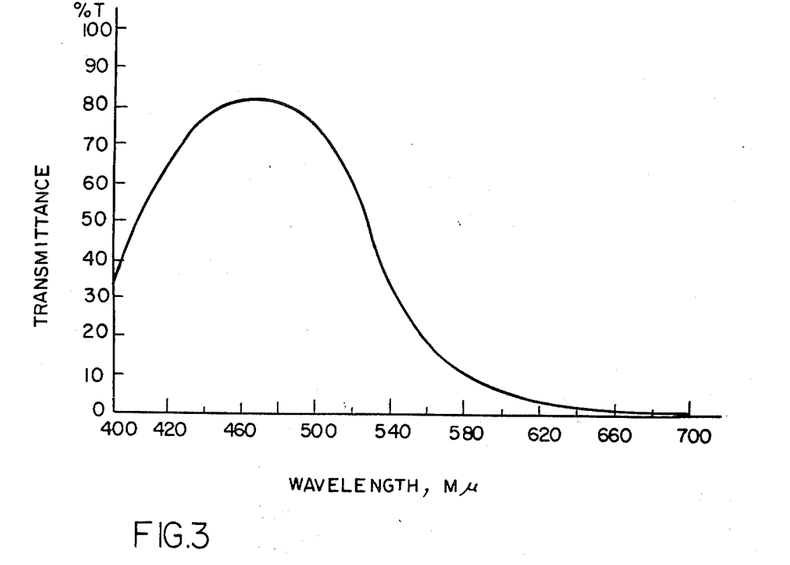
FIG. 3 is a transmittance curve for an electroless copper plating solution.

FIG. 3 of the drawings is the visible spectrum for a copper plating solution of the following composition:

| Copper Sulfate Pentahydrate | 10 grams |
| --- | --- |
| Tartaric Acid | 12 grams |
| Paraformaldehyde | 7 grams |
| Sodium Cyanide | 0.005 grams |
| Sodium Hydroxide (28% solution) | 35 ml |
| Water | To one liter |

Figure 4:
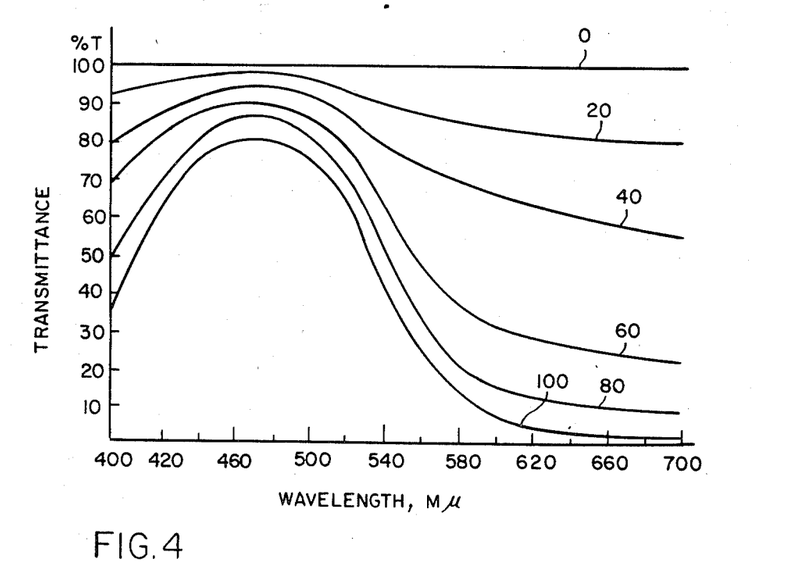
FIG. 4 is a series of transmittance curves for the electroless copper plating solution of FIG. 3 at varying concentrations.

In use of the copper plating solution, complexed copper, the colored component in solution, is consumed by plate-out and accordingly, decreased in concentration. The reduction in concentration does not appreciably change the visible spectrum of light passing through the solution, but rather, the optical density of the solution and hence, the quantum of light passing through the solution—i.e., the intensity of the light passed through the solution. This means that more light at all wave lengths is transmitted through the solution and as the concentration of the copper approaches zero, the perceived color of the solution approaches water white. Thus, in summary, the solution would have an intense or royal blue appearance at a 100% copper concentration and would continue to appear blue as copper became depleted, but intensity of the blue coloration would be reduced until almost all of the copper was plated from solution. The spectrum for a series of copper solutions having decreasing copper contents is illustrated in FIG. 4 of the drawings where there is shown five spectrums for the above copper plating solution with the copper concentration varying between zero percent (100% consumed) and 100% (at full concentration).

A change in the optical density of a solution is perceptible and therefore, may be used as a measure of copper concentration during use of the plating solution, but such change is at best an imprecise measure, particularly at the high copper concentrations used during plating, i.e., the copper concentration is usually maintained between about 60% and 100% of its initial concentration and generally at around 80%. The variation in optical density of the solution within this concentration range is minimal and difficultly observable to the eye, especially where the extinction coefficient for dissolved copper in complex form as in copper plating solution is relatively high.

Figure 5:
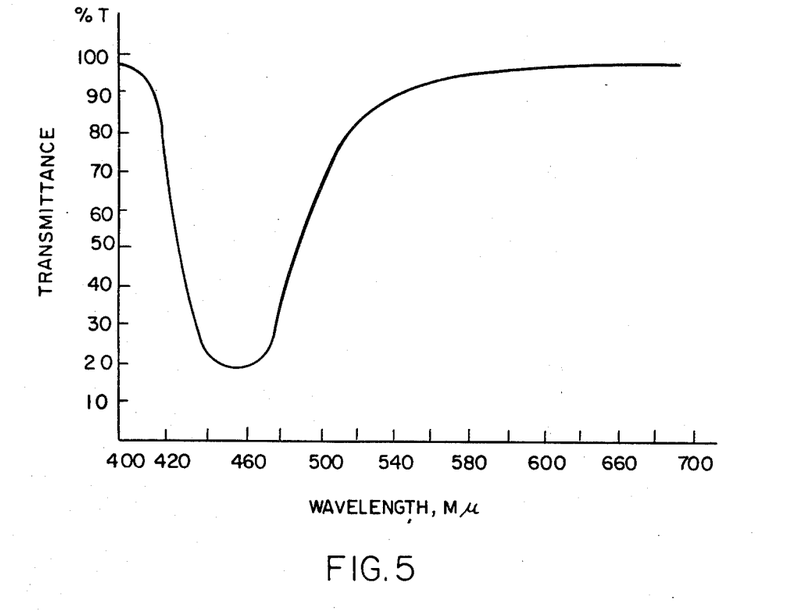
FIG. 5 is a transmittance curve for a yellow colorant.

In accordance with the subject invention, a colorant is used with a solution having its monitored component undergoing variation in concentration with use of the solution. Again, using a copper plating solution for purposes of illustration, with the complexed copper the monitored component consumed with use of the solution, as the solution is used, it changes from intense blue to colorless as a function of copper consumption (see FIG. 4). However, in this illustration, a colorant is used with the copper plating solution such as the idealized yellow colorant having the transmittance curve illustrated in FIG. 5 of the drawings. The colorant has maximum absorption in the blue region of the visible spectrum and maximum transmittance in the yellow through red regions. Hence, white light passing through this colorant is perceived as yellow to yellow-orange. If light passed through both the plating solution during use of the solution and the yellow colorant, the result would be absorption in both the blue and yellow regions and the perceived color would be dependent upon the amount of light absorbed and transmitted in each region, i.e., the optical density of the solution at different portions of the visible spectrum as a consequence of the optical properties of the copper and the colorant. Using the transmittance curves of FIG. 4 (showing transmittance by a copper solution at various concentrations) and FIG. 5 (showing the transmittance curve for an idealized yellow colorant at a fixed concentration), the transmittance curves for light passing through the plating solution and the yellow colorant are illustrated in FIG. 6 of the drawings.

Figure 6:
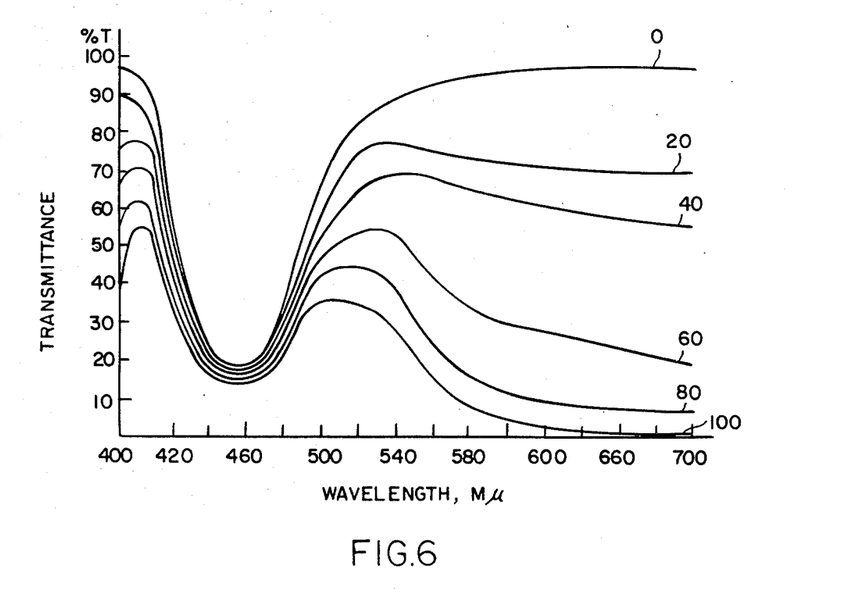
FIG. 6 is a series of transmittance curves that are the summation of the curves of FIG. 4 and the curve of FIG. 5.

FIG. 6 comprises six curves showing transmittance characteristics of the copper plating solution at concentrations ranging between 100% copper and zero percent copper. Comparing FIGS. 4 and 6, at 100% copper concentration, using a yellow colorant, the curve of FIG. 6 exhibits two peaks showing maximum transmittance in the purple and green regions of the visible spectrum with minimum transmittance in the blue and orange regions. It is difficult to accurately predict perceived color from transmittance curves, but practice has demonstrated that the perceived color would be an aquamarine. By comparison, only a single peak is exhibited for the 100% concentration curve of FIG. 4.

With further reference to FIG. 6, as the copper concentration is reduced, there is reduced absorption in the yellow and orange regions resulting in transmission of more yellow and orange light. This results in the appearance of a perceptible color change with the solution changing from aquamarine to green. The shift into the green region is a result of reduced absorption by copper in the orange and yellow regions of the spectrum as a consequence of reduced concentration of copper while the absorption in the blue region of the spectrum by the yellow colorant remains constant. Thus, the amount of yellow light transmitted is increased relative to the amount of blue light transmitted resulting in more yellow and the perception of green. As copper is further reduced in concentration to 60%, more yellow light is passed and the solution appears more green in color. With further reduction in copper, and a further decrease in the absorption within the yellow region, more yellow light is passed and the solution will continue to change in color from green to greenish-yellow to yellow at a zero copper concentration. It should be noted that for an electroless copper solution, the copper content is rarely reduced to zero and the reference to zero concentration is for purposes of illustration only.

The colorant used to cause color change as the monitored component varies in concentration may be external to the solution or contained within the solution provided that transmitted light passes through both the solution and the colorant. In this respect, the colorant liter and the color of the solution is observed while the bath is in use. The bath changes from aquamarine to kelly green over a period of about 1 hour after which time, plating is terminated and a sample of the bath is taken and titrated for copper content. The copper content is found to be about 2 grams per liter or 80% of its original concentration.

Based upon the copper plating equation set forth above, and with a knowledge of the operation of the bath, the copper content together with formaldehyde and hydroxide contents necessary to return the formulation back to original levels can be determined. A replenishment formulation suitable for the above-used plating solution is as follows:

| Additive[1] | Amount Required for Replenishment | |
|---|---|---|
| | Grams per liter | Moles per liter |
| Copper sulfate pentahydrate | 2 | 0.008 |
| Formaldehyde | 1.0 | 0.033 |
| Sodium hydroxide | 1.5 | 0.038 |

[1]As a dry replenisher added in accordance with U.S. Pat. No. 3,870,068. For a liquid replenisher, a factor for volume growth would be included.

The replenishment formulation is not strictly in accordance with the stoichiometry of the plating reaction but rather, the molar ratio of copper to formaldehyde is 1 to 4 rather than 1 to 2 and the molar ratio of the copper to sodium hydroxide is 1 to 5 rather than 1 to 4.

EXAMPLE 2

The procedure of Example 1 is repeated substituting a 0.1% aqueous solution of pylam orange dye for the methyl orange in an amount of 10 ml per liter of solution. The results are similar to those obtained with Example 1, but the change from aquamarine to green was not as easily perceived as with methyl orange. Other dyes that can be used with similar results include yellow dye #5 and yellow dye #6 with results similar to those obtained with the pylam orange, but not as good as the results obtained with methyl orange.

EXAMPLE 3

One liter of a copper plating solution identified as CUPOSIT CP-74 is prepared and 8 ml of a 1% aqueous solution of methyl orange is added. The solution is used to plate epoxy boards in a manner similar to the procedure used for Example 1 with equivalent results.

EXAMPLE 4

An electroless nickel plating solution is prepared having a formulation as follows:

| Nickel sulphate hexahydrate | 35 grams |
|---|---|
| Sodium hypophosphite monohydrate | 15 grams |
| Sodium acetate | 15 grams |
| Potassium iodate | 15 ppm |
| Ammonium hydroxide | to pH about 9.5 |
| Water | to one liter |

Eight ml of a 1% aqueous solution of methyl orange are added to the above solution resulting in only minimal change to the color. The solution is used to plate an epoxy board for 1 hour at a temperature of 195° F. in a manner similar to the procedure of Example 1. During use, the solution changes from blue to a green. After plating for 1 hour, the color of the solution differs substantially from its initial color. A sample is taken after 1 hour of plating, titrated and is found to contain 6 grams of nickel per liter of solution indicating that the nickel was reduced to about 75% of its initial concentration.

EXAMPLE 5

Using the formulation of Example 4 containing methyl orange dye, a sample is taken and diluted with water to a point where the nickel content is 80% of its initial concentration. A color standard is made of the solution at this dilution. Thereafter, an undiluted fresh sample is used to plate nickel for a time sufficient for the color of the plating solution to match the color standard. This takes about 50 minutes. At the point when the color of the solution matches the color of the standard, a sample is taken titrated and found to contain 6.4 grams per liter of nickel or 81.5% of its initial concentration.

EXAMPLE 6

An etching solution is prepared having a formulation as follows:

| Sulphuric acid (50%) | 200 ml |
|---|---|
| Hydrogen peroxide (35%) | 100 ml |
| Phenol sulfonic acid | 16 grams |
| Water | to one liter |

At a temperature of 120° F., the above etchant dissolves all of the copper off of four 1.4 mil copper clad epoxy substrates measuring 3 inches by 3 inches in 13 minutes resulting in a solution containing about 7.4 grams per liter of copper which is blue in appearance. The solution is used in this manner for repeated etching of two sets of four epoxy clad substrates to provide a solution containing about 15 grams of dissolved copper.

In accordance with this invention, 10 ml of a 1% aqueous solution of methyl orange is added to a fresh etchant. The etchant turns bright red (not yellow because of the low pH of the etchant). The etchant is then used to etch copper and is periodically sampled and titrated for copper content until the dissolved copper content reaches 15 grams per liter. During use, the etchant gradually changes from red to reddish-purple to purple as copper is dissolved. A color standard matching the color of the etchant is prepared at a dissolved copper content of 15 grams per liter. Thereafter, a fresh etchant containing the methyl orange is prepared and used to etch copper in the manner described above for a time sufficient for the color of the etchant to match that of the color standard. A sample is then taken, titrated and found to contain about 14 grams of copper per liter of solution. At this point, the etchant is rejuvenated by removal of copper such as by electrolytic plating of the copper and replenished with fresh peroxide and sulfuric acid.

We claim:

1. A process for monitoring the concentration of a plating metal in an electroless plating solution during use of the same and plate-out of the metal, said process comprising the steps of plating metal from said solution observing light passing through the solution containing a colorant, which observed solution remains capable of depositing metal over a catalytic surface in the absense of electricity, where the colorant is selected to absorb and transmit light in portions of the spectrum differing from those portions of the spectrum where the plating metal in solution absorbs and transmits light and where the colorant and the plating metal in solution have maximum transmittance at wavelengths separated by at least 50 millimicrons and the wavelength of the maximum transmittance of the plating metal in solution is within 50 millimicrons of the wavelength for the maximum absorption by the colorant; whereby the perceived color of the plating solution will change as the concentration of the plating metal changes, and correlating the color of the solution with the concentration of the plating metal.

2. The process of claim 1 where the optical density of the color component of the solution due to the colorant is essentially constant during plate-out of metal from the plating solution.

3. The process of claim 1 where the wavelengths for maximum transmittance are separated by at least 100 millimicrons and the wavelengths for maximum transmittance by the plating metal in solution is substantially coincident with the wavelength for maximum absorption by the colorant.

4. The process of claim 2 where the colorant transmits light in the yellow region of the visible spectrum and has maximum absorption in the blue region.

5. The process of claim 2 where the colorant is external to the plating solution.

6. The process of claim 5 where the colorant is a filter.

7. The process of claim 6 where the filter is a yellow filter.

8. The process of claim 2 where the colorant is within the plating solution.

9. The process of claim 2 where the optical density of the colorant remains substantially constant by use of a colorant having a substantially constant concentration in solution.

10. The process of claim 9 where the colorant is a yellow dye.

11. The process of claim 9 where the colorant is methyl orange.

12. The process of claim 2 where the correlation between the color of the solution and the concentration of the plating metal is made by comparison of the color of the solution with color standards.

13. The process of claim 12 where the color standard used is the color of the plating solution when the plating metal is reduced to between about 60% and 80% of its initial concentration.

14. The process of claim 10 where the concentration of the colorant in solution is sufficient to cause an easily perceivable color change when the plating metal is reduced to about 60% to 80% of its initial concentration, but insufficient to cause a substantial color change when the plating metal is at 100% concentration.

15. A process for monitoring the concentration of copper in an electroless copper plating solution during use of the same and plate-out of copper, said process comprising the steps of plating copper from solution, observing light passing through the plating solution containing a colorant, which observed solution remains capable of depositing metal over a catalytic surface in the absence of electricity, where the colorant absorbs and transmits light in portions of the spectrum differing from those portions of the spectrum where dissolved copper in solution absorbs and transmits light and where the colorant and copper in solution have maximum transmittance at wavelengths separate by at least 50 millimicrons and the wavelength for maximum transmittance for copper is within 50 millimicrons of the wavelength for maximum absorption for the colorant; whereby the perceived color of the plating solution will change as the concentration of copper changes, and correlating the color of the solution with the concentration of copper in solution.

16. The process of claim 15 where the optical density of the color component of the solution due to the colorant is essentially constant during plate-out of copper from the plating solution.

17. The process of claim 15 where the wavelength for maximum transmittance are separated by at least 100 millimicrons and the wavelength for maximum transmittance by copper in solution is substantially coincident with the wavelength for maximum absorption of the colorant.

18. The process of claim 16 where the colorant has maximum transmittance in the yellow regions of the visible spectrum and maximum absorption in the blue region.

19. The process of claim 16 where the colorant is a filter external to the plating solution.

20. The process of claim 19 where the filter is yellow.

21. The process of claim 16 where the colorant is within the plating solution and its optical density is held constant by maintaining its concentration constant.

22. The process of claim 21 where the colorant is a yellow dye.

23. The process of claim 16 where the correlation between the color of the solution and the concentration of the copper is made by comparison of the color of the solution with green color standards that match the color of the solution when the copper concentration in solution is reduced to between about 60% and 80% of its initial concentration.

24. The process of claim 16 where the concentration of the colorant in solution is sufficient to cause an easily perceivable color change when the copper in solution is reduced to about 60% to 80% of its initial concentration but insufficient to cause a substantial color change when the copper in solution is at 100% concentration.

25. The process of claim 23 including as an additional step, replenishing the copper and other solution components to substantially their initial concentration when the color of the solution matches the color of the color standard.

26. A process for monitoring the concentration of a dissolved component in solution which monitored component in solution changes in concentration during use of the solution and imparts a color to the solution when dissolved therein, said process comprising the steps of using said solution to change the concentration of the monitored component, observing light passing through the solution containing a colorant, which observed solution remains capable of use, where the colorant remains of a substantially constant optical density during the use of the solution and absorbs and transmits light in portions of the spectrum differing from those portions of the visible spectrum where the monitored component in solution absorbs and transmits light and where the colorant and monitored component in solution have maximum transmittance at wavelengths separated by at least 50 millimicrons and the wavelength for maximum transmittance for the monitored component is within 50 millimicrons of the wavelength for maximum absorption for the colorant; whereby the perceived color of the solution will change as the concentration of the monitored component changes, and correlating the color of the solution with the concentration of the monitored component.

27. The process of claim 26 where the colorant is a filter external to the solution.

28. The process of claim 26 where the colorant is within the solution.

29. The process of claim 26 where the colorant is a dye which does not adversely react with the remaining ingredients in solution.

30. The process of claim 26 where the correlation between the color of the solution and the concentration of the monitored component is made by comparison of the color of the solution with color standards.

31. The process of claim 29 where the concentration of the colorant in solution is sufficient to cause an easily perceivable color change when the monitored component is changed in concentration to a predetermined level.

32. The process of claim 26 where the solution is a solution for etching metals.

* * * * *